United States Patent [19]

Yamamuro et al.

[11] Patent Number: 4,508,816
[45] Date of Patent: Apr. 2, 1985

[54] METHOD FOR BLEACHING COLOR PHOTOSENSITIVE MATERIAL

[75] Inventors: Kiyohiko Yamamuro; Shigeo Hirano; Isamu Itoh; Yasuo Iwasa, all of Kanagawa, Japan

[73] Assignee: Fuji Photo Film Co., Ltd., Kanagawa, Japan

[21] Appl. No.: 544,155

[22] Filed: Oct. 21, 1983

[30] Foreign Application Priority Data

Oct. 21, 1982 [JP] Japan .................................. 57-185680
Jan. 11, 1983 [JP] Japan .................................... 58-2522

[51] Int. Cl.³ .......................... G03C 7/00; G03C 5/44
[52] U.S. Cl. ................................... 430/393; 430/430; 430/461; 430/564
[58] Field of Search .............. 430/393, 564, 566, 430, 430/461

[56] References Cited

U.S. PATENT DOCUMENTS 3,772,020 11/1973 Smith .................................. 430/393
3,893,858 7/1975 Wabnitz .............................. 430/393

Primary Examiner—Mary E. Downey
Attorney, Agent, or Firm—Sughrue, Mion, Zinn, Macpeak, and Seas

[57] ABSTRACT

An improved method for bleaching color photosensitive materials with a persulfate is provided. This method is free of offensive odors, can bleach efficiently color photosensitive materials containing a large amount of silver by using a persulfate, and can effectively bleach color photosensitive materials having colloidal silver layers by using a persulfate. The color photosensitive material used in the present invention contains at least one of the compounds represented by the formula I, salts thereof and precursors thereof:

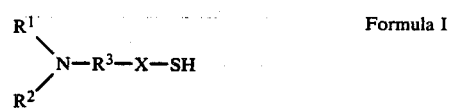

Formula I where $R^1$ and $R^2$ each independently represents a hydrogen atom, or an aliphatic residue and $R^1$ and $R^2$ may form a ring together with the N atom; $R^3$ represents —$R^4$— or —$R^4$—S, said —$R^4$— being a divalent aliphatic residue; and X represents a divalent heterocyclic ring residue containing at least one atom selected from the group consisting of a nitrogen atom, an oxygen atom, and a sulfur atom.

23 Claims, No Drawings

METHOD FOR BLEACHING COLOR PHOTOSENSITIVE MATERIAL

FIELD OF THE INVENTION

The present invention relates to a method for bleaching a silver halide color photosensitive material (referred to as color photosensitive material hereinafter). More particularly, it relates to a method which offers improved bleachability of a photosensitive material with a persulfate.

BACKGROUND OF THE INVENTION

The processing of color photosensitive materials comprises basically the color development process and the desilvering process. The exposed color photosensitive material first undergoes the color development process, in which the silver halide is reduced to give silver by the color developing agent and the oxidized color developing agent reacts with the coupler to form a dye image. Then the color photosensitive material undergoes the desilvering process, in which the silver formed in the preceding process is oxidized by the action of an oxidizing agent (commonly called a bleaching agent). Finally the oxidized silver is solbilized and removed from the photosensitive material by a chelating agent for silver ions (commonly called a fixing agent). As a result, a dye image is formed on the color photosensitive material. In the actual development processing, the above-mentioned main processes—color development and desilvering—are accompanied by auxiliary processes to ensure the photographic and physical properties of the image and to preserve the image for a long time. They include, for example, the hardening bath which prevents the sensitive layer from getting excessively soft during processing, the stopping bath which effectively stops the development reaction, the stabilizing bath which stabilizes the image, and the bath to remove the backing layer of the base.

The desilvering process may be accomplished in a single bath which contains a bleaching agent and a fixing agent. It may also be accomplished in two separate baths for bleaching and fixing.

Bleaching agents in general use include red prussiate, potassium bichromate, ferric ion complex salt, and persulfate. A bleaching solution of red prussiate performs outstanding bleaching action; but it has a disadvantage that the ferricyanide ions and ferrocyanide ions, which are reduced forms of the ferricyanide ions, are discharged from the processing equipment and form highly toxic cyanide compounds upon photooxidation. Therefore, there has been a demand for a new bleaching agent that will replace red prussiate.

A ferric ion commplex salt is used as a bleaching agent of the bleach-fix bath for color photographic paper. (See German Pat. Nos. 866,605 and 966,410, and British Pat. Nos. 746,567, 933,088, and 1,014,396.) The bleaching solution or bleach-fix solution containing a ferric ion complex salt is weak in oxidation. Therefore, it takes a long time for the processing of color photosensitive materials which contain silver halides in high concentrations and also contain silver iodobromide.

Since bleaching with red prussiate or a ferric ion complex salt causes water pollution, bleaching with no metallic ions or bleaching with a persulfate is preferable. However, the persulfate bleaching solution is weaker in bleaching power than ferric ion complex salts and takes an extremely long time for bleaching. Thus there has been a demand for a method for accelerating the bleaching with a persulfate which can be applied to high-speed color photosensitive materials containing a large amount of silver halides.

The bleaching with a persulfate is accelerated by adding an amino compound to the treating bath such as the bleaching bath, the bleach-fix bath, or the prebath thereof, according to the conventional methods as disclosed in U.S. Pat. Nos. 3,772,020 and 3,893,858 and "Research Disclosure" No. 15704.

These methods still take a considerably long time for complete bleaching. Moreover, the addition of an amino compound to the bath is not preferable because it usually gives off an offensive odor. In addition, these methods are unable to bleach completely the color photosensitive materials having colloidal silver layers (such as yellow filter layer and antihalation layer) and hence containing a large amount of silver.

SUMMARY OF THE INVENTION

Accordingly, it is an object of this invention to provide a method which offers improved bleachability in photosensitive materials with a persulfate.

It is another object of this invention to provide a method which offers improved bleachability in color photosensitive materials with a persulfate without the possibility of generation of offensive odors.

A further object of this invention is to provide a method for efficiently bleaching color photosensitive materials containing a large amount of silver by using a persulfate.

Still a further object of this invention is to provide a method for efficiently bleaching color photosensitive materials having colloidal silver layers by using a persulfate.

The objects of the invention are achieved by a method for bleaching color photosensitive materials which comprises bleaching, after exposure and color development, a color photosensitive material with a processing solution containing a persulfate, said color photosensitive material containing at least one member of the compounds represented by the formula I, the salts thereof, and the precursors which form said compounds upon cleavage in an acid or alkaline processing solution.

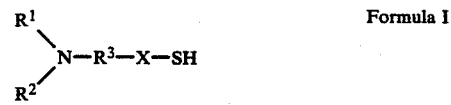

Formula I where $R^1$ and $R^2$ each independently represents a hydrogen atom or an aliphatic residue and $R^1$ and $R^2$ may for a ring together with the N atom; $R^3$ represents $-R^4-$ or $-R^4-S-$, said $-R^4-$ being a divalent aliphatic residue; and X presents a divalent heterocyclic ring residue containing at least one atom selected from the group consisting of a nytrogen atom, an oxygen atom, and a sulfur atom.

DETAILED DESCRIPTION OF THE INVENTION

In the formula I $R^1$ and $R^2$ each represents hydrogen atom and an aliphatic hydrocarbon residue. The aliphatic hydrocarbon residue preferably has 1-12 of carbon atoms and includes an alkyl group, an alkenyl group, and an alkynyl group which may be substituted.

The alkyl groups include methyl group, ethyl group, propyl group, butyl group, hexyl group, decyl group, dodecyl group, isopropyl group, sec-butyl group, and cyclohexyl group. The alkenyl groups include allyl group, 2-butenyl group, 2-hexsenyl group, and 2-octenyl group. The alkynyl groups include propargyl group and 2-pentynyl group. The substituents includes a phenyl group, a phenyl group substituted with for example an alkyl group preferably having 1 to 5 carbon atoms, an alkoxy group, an alkylthio group, hydroxyl group, carboxyl group, sulfo group, an alkylamino group, and an amido group (the alkyl moiety in these substituents preferably has 1-5 carbon atoms). $R^1$ and $R^2$ may combine to form a five-membered or six-membered heterocyclic ring containing one nitrogen atom or containing at least one nitrogen atom and/or oxygen atom in addition to one nitrogen atom. Examples of such heterocyclic rings include

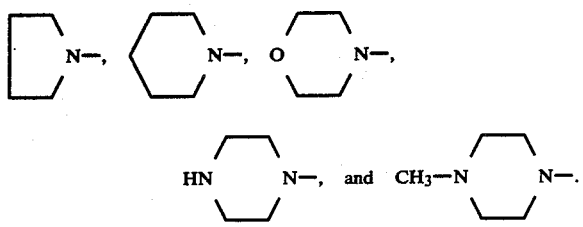

The preferred examples of $R^1$ and $R^2$ include hydrogen atoms and an alkyl group having 1-3 carbon atoms. More preferable among them are hydrogen atoms and methyl groups and ethyl groups.

$R^3$ represents $-R^4-$ or $-R^4-S-$, where $R^4$ represents a divalent aliphatic residue, preferably a saturated or unsaturated linear or branched aliphatic hydrocarbon group having 1-6 carbon atoms. $R^4$ may have an ether bond in the carbon chain of these residue. Examples of $R^4$ include $-CH_2-$, $-CH_2CH_2-$, $-(CH_2)_3-$, $-(CH_2)_4-$, $-(CH_2)_6-$, $-CH_2CH=CHCH_2-$, $-CH_2C\equiv CCH_2-$, and

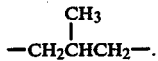

More preferably $R^4$ have a carbon number of 2 to 4. More preferred examples of $R^4$ are $-CH_2CH_2-$ and $-CH_2CH_2CH_2-$. $R^3$ is preferably $-R^4-S-$.

X represents a five-membered and six-membered heterocyclic ring containing at least one nitrogen, oxygen, or sulfur. This heterocyclic ring may be condensed with a benzene ring. Examples of such heterocyclic rings include azole rings such as tetrazole, triazole, thiadiazole, oxadiazole, imidazole, thiazole, oxazole, benzimidazole, benzothiazole, and benzoxazole rings. Especially preferable among them are tetrazole and thiadiazole rings. They may be substituted by an alkyl-substituted amino group, etc.

Salts of the compound represented by formula I includes alkali metal salts [salts of $Na^+$, $K^+$, $Li^+$, etc.], alkaline earth metal salts [salts of $Ca^{++}$, $Mg^{++}$, etc.], heavy metal salt [salts of $Pb^{++}$, $Co^{++}$, $Ag^+$, etc.], quaternary ammonium salts containing an alkyl and/or aralkyl group, preferably containing 4–30 carbon atoms, such as $(CH_3)_4N^+$, $(C_2H_5)_4N^+$, $(C_4H_9)_4N^+$, $C_6H_5CH_2N^+(CH_3)_3$, and $C_{16}H_{33}P^+(CH_3)_3$, quaternary phosphonium salts containing an alkyl and/or aralkyl group preferably containing 4–30 carbon atoms such as $C_{16}H_{33}P^+(CH_3)_3$, $C_6H_5CH_2P^+(CH_3)_3$, etc., and strong acid salts such as hydrochloride, sulfate, p-toluenesulfonate, and methanesulfonate.

The precursor of the relevant compound, which cleaves under the acidic or alkaline condition in the processing liquid, has a group (instead of $-SH$ in the formula I) such as a mono- or di-thiocarbamate group preferably substituted with one or two alkyl groups having 1-5 carbon atoms or with one or two phenyl groups at N [such as $-SCONHCH_3$, $-SCON(C_2H_5)_2$, $-SCSNHC_2H_5$ and

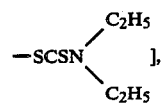

2-substituted ethylthio group preferably substituted with a cyano group or an acyl group having 2-6 carbon atoms, [such as $-SCH_2CH_2CN$ and $-SCH_2CH_2COCH_3$], and benzylthio group preferably substituted with a hydroxyl group or acyl group having 2-6 carbon atoms, such as

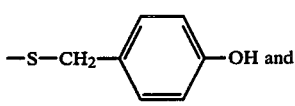

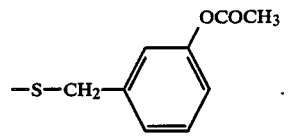

Examples of the precursor further include compounds obtained by dimerization of a compound represented by formula I to form a disulfide group [$-S-S-$].

The compound of formula I, the salt thereof, and the precursor thereof are collectively called "the compound of formula I" hereinafter.

The examples of the compound of formula Ia include the following:

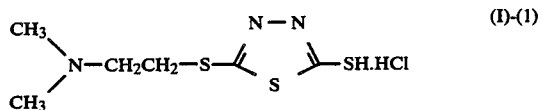
(I)-(1)

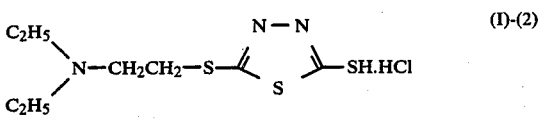
(I)-(2)

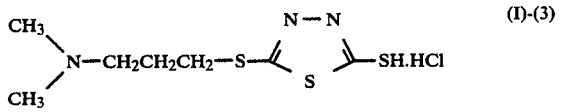
(I)-(3)

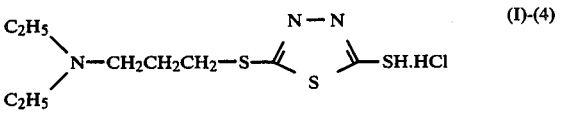
(I)-(4)

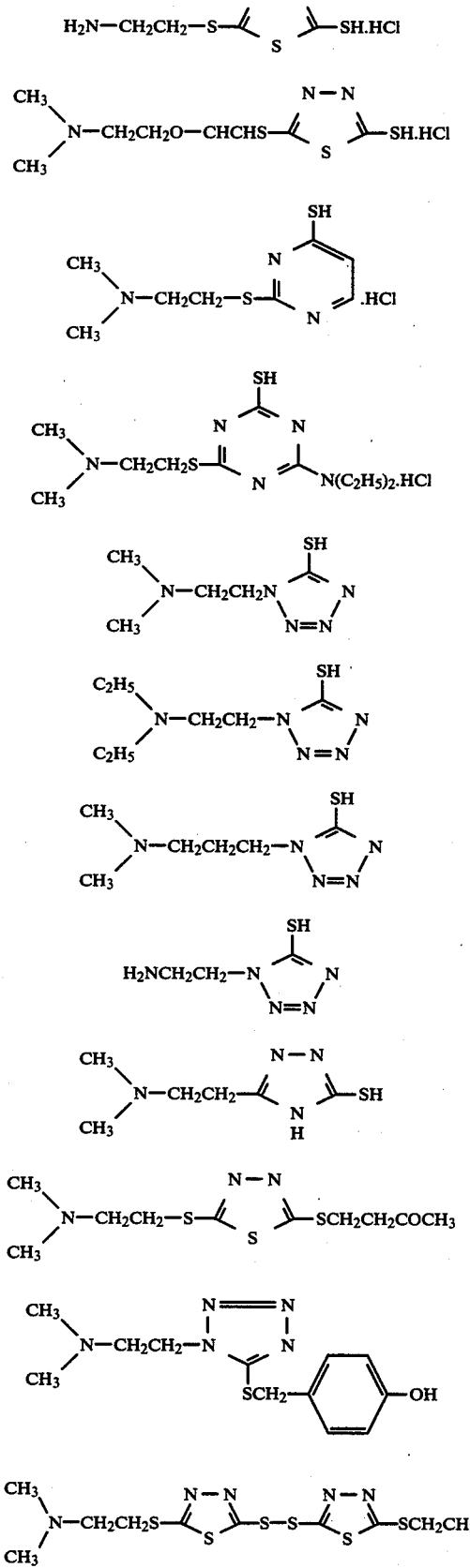

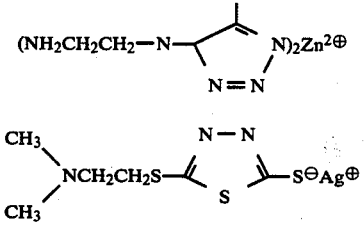

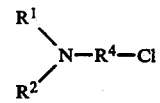

The compound of formula I in which $R^3$ is $-R^4-S$ can be synthesized by reacting $$R^1\!\!\diagdown\!\!\!\!\phantom{N}\atop R^2\!\!\diagup\!\!\!\phantom{N}N-R^4-Cl$$

with a dimercaptosubstituted heterocyclic ring. The compound of formula I in which $R^3$ is $-R^4-$ can be synthesized by introducing a heterocyclic ring through the ring-forming reaction as disclosed in Japanese Patent Laid-Open Nos. 1475/1976 and 50169/1978.

SYNTHESIS EXAMPLE 1

Syntheses of the compounds of formulae I-1 to I-5

15 g (0.1 mole) of commercially available 2,5-dimercapto-1,3,4-thiadiazole and 14.4 g (0.1 mole) of dimethylaminoethylchloride hydrochloride were dispersed into 75 ml of n-butanol contained in a 300-ml three-neck flask. While stirring at 80° C., 7.9 g (0.1 mole) of pyridine was added dropwise. The reaction was continued under reflux for 2 hours. The reaction liquid was cooled with ice and separated crystals were filtered off. After recrystallization from ethanol/water (volume ratio: 19/1), there was obtained 22.6 g (yield 79%) of the compound of formula I-1.

m.p.: 161° to 163° C.

In the same way as above, by using corresponding amine compounds, there were obtained the compounds of formulas I-2, I-3, I-4, and I-5, in almost the same yield.

m.p. of I-2: 184° to 186° C.
m.p. of I-3: 149° to 152° C.
m.p. of I-4: 172° to 175° C.
m.p. of I-5: 228° to 229° C.

SYNTHESIS EXAMPLE 2

Syntheses of the compounds of formula I-9 to I-12

88 g (1 mole) of dimethylaminoethylamine, 101 g (1 mole) of triethylamine, and 400 ml of tetrahydrofuran were mixed in a 1-liter three-neck flask. With ice cooling, 83.6 g (1.1 moles) of carbon disulfide was added dropwise. After stirring was continued for 3 hours at 5° C., 217 g (1.05 moles) of dicyclohexylcarbodiimide was added, and stirring was continued further for 2 hours. After reaction was complete, 400 ml of benzene was added to remove insolubles. The reaction liquid was washed with 2N-HCl aqueous solution and water, and then dried with Glauber's salt. After the removal of the solvent, there was obtained about 110 g of 2-dimethylaminoethyl isothiocyanate in the form of crude oil. Without subjecting to purification the thus obtained product was dispersed into a mixture of 400 ml of water and 150 ml of ethanol contained in a 1-liter three-neck flask, followed by stirring at 70° to 75° C. for 5 hours in a water bath. The reaction liquid was cooled to 10° C. and 400 ml of 2N HCl was added. Separated crystals were filtered off. After recrystallization from isopropanol, there was obtained 94 g (yield: 45%) of the compound of formula I-9.

m.p.: 218° to 219° C.

In the same way as above, by using corresponding amine compounds, there were obtained the compounds of formulas I-10, I-11, and I-12, in almost the same yield.

m.p. of I-10: 131° to 132° C.
m.p. of I-11: 192° to 193° C.
m.p. of I-12: 190° to 192° C.

The compound of formula I is added to at least one of the layers constituting the color photosensitive material. Usually, it is added in an amount of $1 \times 10^{-7}$ to $1 \times 10^{-3}$ mole, and preferably $1 \times 10^{-6}$ to $1 \times 10^{-4}$ mole, per 1 m² of support.

The bleaching method of this invention can be applied to various kinds of color photosensitive materials such as color positive film, color paper, color negative film, and color reversal film with or without coupler. The bleaching method of this invention can be advantageously applied to a high-silver photosensitive materials containing a total silver quantity more than 30 mg/100 cm², and preferably 40 mg/100 cm². The bleaching method of this invention can be most effectively applied to the photosensitive material made up of a support, antihalation layer of colloidal silver, intermediate layer, red sensitive layer, intermediate layer, green sensitive layer, yellow filter layer of colloidal silver, blue sensitive layer, and protective layer. (The intermediate layers may be omitted.) Each of the red sensitive layer, green sensitive layer, and blue sensitive layer may be divided into a low sensitive layer and a high sensitive layer. The layer structure may be such that at least one of the red sensitive layer, the green sensitive layer, and the blue sensitive layer is divided into three sublayers as disclosed in Japanese Patent Publication No. 15495/1974 (corresponding to U.S. Pat. No. 3,843,363); the layers are divided into the high-speed emulsion layer unit and low speed emulsion layer unit as disclosed in Japanese Patent Application No. 49027/1976, and the layer structure as disclosed in West German Laid Open Patent Application Nos. 2,622,922 (corresponding to U.S. Pat. No. 4,129,446), 2,622,923 (corresponding to U.S. Pat. No. 4,186,016), 2,622,924 (corresponding to British Pat. No. 1,560,965), 2,704,826, and 2,704,797.

The compound of formula I of this invention is preferably added to the silver halide emulsion layer, protective layer, subbing layer, intermediate layer, yellow filter layer, and antihalation layer. More suitably, it is added to a layer containing colloidal silver. Most suitably, it is added to the anti-halation layer of colloidal silver which is most difficult to bleach.

For effective bleaching with a persulfate salt, the compound of formula I may be used in combination with at least one compound of formula II below or a salt thereof or a precursor which forms the compound upon cleavage under an alkaline condition. The compound of formula II, the salt thereof, and the precursor thereof are collectively called "the compound of formula II" hereinafter. This compound prevents the fogging of color photosensitive materials induced by colloidal silver with time during storage. Unlike the conventional compound called stabilizer or antifoggant, the compound of formula II does not interfere with desilvering. Therefore it can be advantageously used in combination with the compound of formula I.

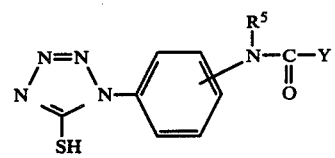

Formula II where Y represents $-NR^6R^7$ or $-OR^8$; $R^5$, $R^6$, and $R^7$ each represents hydrogen atoms, substituted or unsubstituted aliphatic groups, or substituted or unsubstituted aromatic groups; and $R^8$ represents a substituted or unsubstituted aliphatic group or a substituted or unsubstituted aromatic group. $R^6$ and $R^7$ may be the same or different, or may form a five-membered ring or six-membered ring together with the N atom.

The compound of formula II is described in more detail in the following.

The aliphatic group in $R^5$, $R^6$, $R^7$, and $R^8$ includes alkyl groups or alkenyl groups preferably containing up to 18 carbon atoms such as methyl group, ethyl group, n-propyl group, n-butyl group, t-butyl group, n-pentyl group, n-hexyl group, cyclohexyl group, n-octyl group, n-dodecyl group, n-octadecyl group, n-octadecyl group, and allyl group.

The aromatic group in $R^5$, $R^6$, $R^7$, and $R^8$ includes aryl groups preferably having 6-20 carbon atoms, such as phenyl group and naphthyl group.

$R^6$ and $R^7$ form, together with N, a ring preferably having 2-10 carbon atoms, which may contain at least one of O, N, and S in addition to the N atom of the amino group.

Examples of $R^6$ and $R^7$ include $-(CH_2)_4-$, $-(CH_2)_5-$, $-(CH_2)_6-$, $-CH_2CH_2OCH_2CH_2-$, and

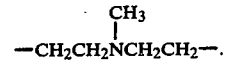

Examples of the substituent of $R^5$, $R^6$, $R^7$ and $R^8$ include an alkoxy group (such as methoxy group and ethoxy group), halogen (such as chlorine and bromine), an alkyl group (such as methyl group and ethyl group), phenyl group, an alkoxycarbonyl group (such as ethoxycarbonyl group), an acyl group (such as acetyl group), an acyloxy group (such as acetyloxy group), cyano group, nitro group, an alkylthio group (such as methylthio group), an amido group (such as acetamide group), and a sulfoneamide group (such as methane sulfoneamide group). The alkyl moiety in these groups preferably have 1-5 carbon atoms.

$R^5$ preferably is a hydrogen atom, an alkyl group having 1-3 carbon atoms, and a phenyl group. Most preferable among them are a hydrogen atom and a methyl group.

$R^6$ and $R^7$ each preferably is hydrogen atom, an alkyl group having 1-6 carbon atoms, and a phenyl group. Most preferably among them are a hydrogen atom, methyl group, ethyl group, and n-propyl group.

$R^8$ preferably is an alkyl group of carbon number 1 to 6 and a phenyl group. Most preferable among them are a methyl group, ethyl group, n-propyl group, and phenyl group.

The salt of the compound represented by formula II includes alkali metal salts [Na+, K+, Li+, etc.], alkaline earth metal salts [$Ca^{++}$, $Mg^{++}$, etc.], Al and heavy metal salts [$Al^{+++}$, $Ni^{++}$, $Zn^{++}$, $Cu^{++}$, $Ag^+$, etc.], quaternary ammonium salts [$NH_4^+$, $(CH_3)_4N^+$, $(C_4H_9)_4N^+$, $n\text{-}C_{12}H_{25}N^+(CH_3)_3$, and $n\text{-}C_{16}H_{33}N^+(CH_3)_3$], and quaternary phosphonium salts [$(C_4H_9)_4P^+$ and $C_6H_5CH_2P^+(CH_3)_3$].

As is known well, an additive for a photographic material, having a —SH group can be used in the form of a precursor which cleaves under an alkaline condition. Therefore, the precursor can be produced when the hydrogen atom of the —SH group in the compound of formula II is substituted with a group to form a group which cleaves under an alkaline condition to form —SH. Examples of such a group include a reverse Michael type group as disclosed in U.S. Pat. Nos. 3,888,677, 4,009,029, and 4,307,175; a quinone methide type group as disclosed in U.S. Pat. Nos. 3,674,478, 3,932,480, 3,993,661, and 4,350,754, and Japanese Patent Laid-Open Nos. 135944/1982, 135745/1982, and 136640/1982; and a ring cleaving type group as disclosed in U.S. Pat. Nos. 4,310,612, 4,350,752, and 4,335,200. The scope of this invention is not limited to them; but it embraces any group which liberates the compound represented by formula II during the development processing.

Useful examples of the compound of formula II are shown below.

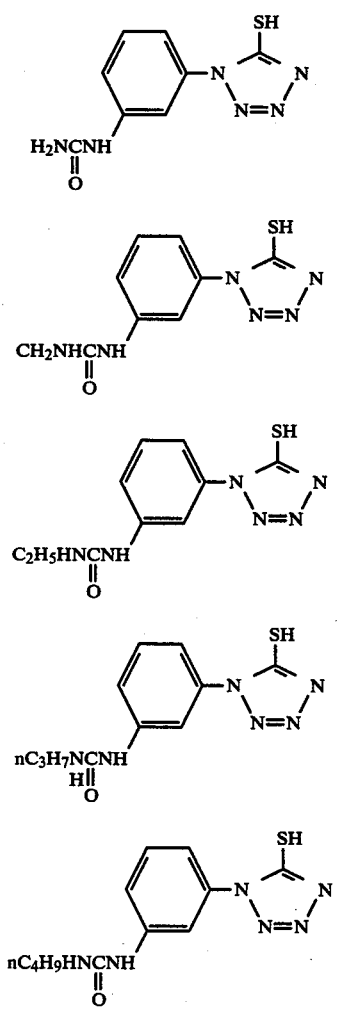
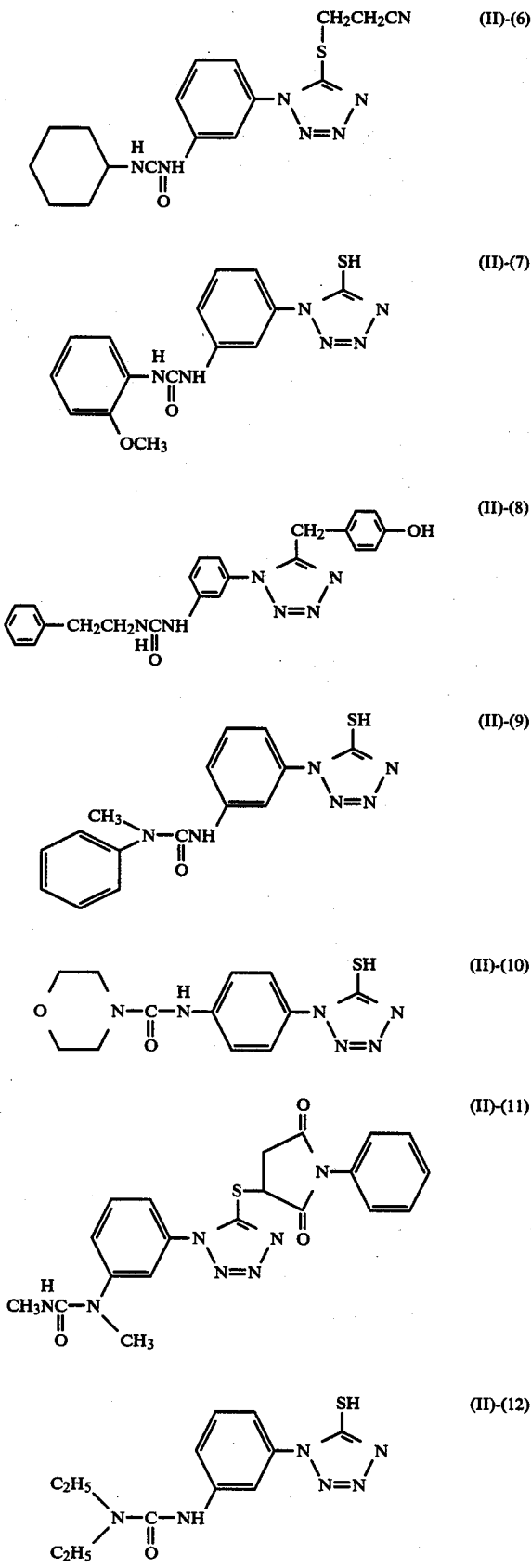

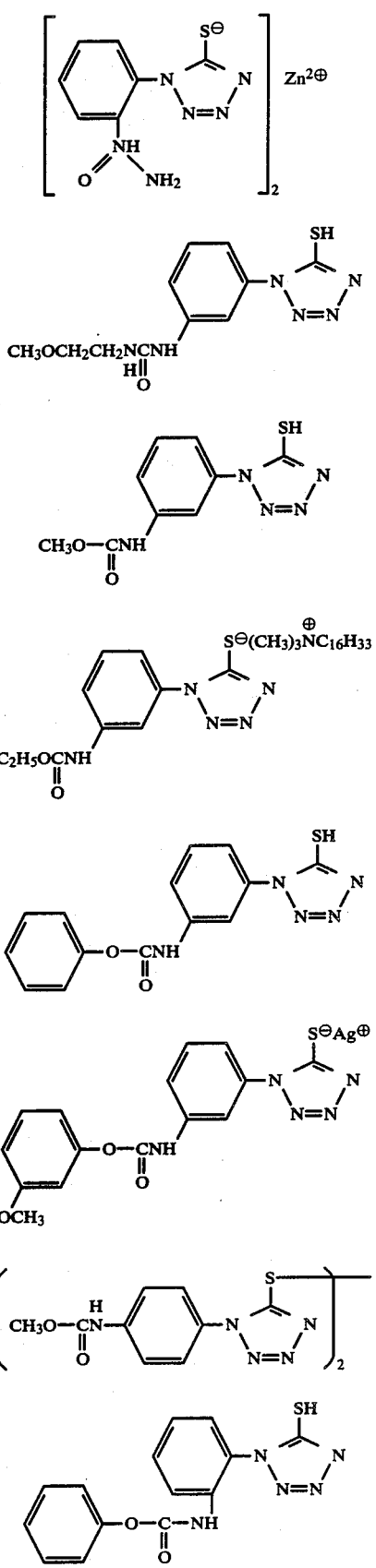

These compounds are readily synthesized by reacting 1-aminophenyl-5-mercaptotetrazole with isocyanic acid, isocyanate, N,N-di-substituted-carbamoyl halide, or halocarbonate ester in the presence of an organic base (such as triethylamine and pyridine). The 1-aminophenyl-5-mercaptotetrazole is obtained by hydrolyzing amide-substituted 1-amidephenyl-5-mercaptotetrazole such as those disclosed in Japanese Patent Laid-open Nos. 37436/1975 and 3231/1976; and U.S. Pat. Nos. 3,295,976 and 3,376,310 with a strong acid such as hydrochloride acid.

The syntheses of these compounds are described in detail in Japanese Patent Application Nos. 193,832/1981 (corresponding to EPC Published Patent Application No. 81689A (Applicant: Fuji Photo Film Co., Ltd.), 179378/1982 and 230912/1982. Some examples of the syntheses are given below.

SYNTHESIS EXAMPLE 1

5-Mercapto-1-(3-ureidophenyl)-1,2,3,4-tetrazole (Formula II-1)

49.8 g of 1-(3-aminophenyl)-5-mercaptotetrazole hydrochloride was dispersed in 380 ml of water, with stirring at room temperature. 42 ml of triethylamine was added dropwise. 180 ml of acetic acid was added. A solution prepared by dissolving 26 g of sodium cyanate in 180 ml of water was added dropwise. The resulting solution was stirred for 6 hours at room temperature. The crystals which had separated out were filtered off and rinsed with water. The crystals were then dissolved in a mixture of methanol and triethylamine. After filtration, the solution was made acidic with hydrochloric acid. The crystals which had separated out were filtered off and rinsed with methanol. Thus there was obtained 33.7 g (yield 71.3%) of the above-mentioned compound.

m.p.: 226° to 230° C.

SYNTHESIS EXAMPLE 2

5-Mercapto-1-[3-(3-methylureido)phenyl]-1,2,3,4-tetrazole (Formula II-2)

24.9 g of 1-(3-aminophenyl)-5-mercaptotetrazole hydrochloride and 13.0 g of triethylamine were dispersed in 120 ml of acetonitrile. 8.5 g of methylisocyanate was added dropwise. After stirring for about 5 hours at room temperature, 700 ml of water was added. The solution was made acidic with hydrochloric acid. The crystals which had separated out were filtered off and rinsed with water. The crystals were then dissolved in a mixture of methanol and triethylamine. After filtration, the solution was made acidic with hydrochloric acid. The crystals which had separated out were filtered off and rinsed with methanol. Thus there was obtained 16.4 g (yield 65.6%) of the above-mentioned compound.

m.p.: 215° to 216° C.

By repeating the above process, with the methyl isocyanate replaced by an alkyl isocyanate corresponding to the compound of formulae II-3, II-4 and II-5, respectively, there were obtained the compounds of formulae II-3 to II-5.

m.p. of II-3: 202° 5o 204° C.
m.p. of II-4: 197° to 198° C.
m.p. of II-5: 171° to 172° C.

SYNTHESIS EXAMPLE 3

1-[3-(3-diethylureido)phenyl]-5-mercapto-1,2,3,4-tetrazole (Formula II-12)

23 g of 1-(3-aminophenyl)-5-mercaptotetrazole and 32 g of pyridine were dispersed in 220 ml of acetonitrile. 16 g of N,N-diethylcarbamoyl chloride was added dropwise. After heating under reflux for 1.5 hours, 200 ml of water was added and the solution was extracted with ethyl acetate. By condensation and recrystallization from 250 ml of acetonitrile, there was obtained 15 g of the object product (yield 51%).

m.p.: 184° to 185° C.

SYNTHESES EXAMPLE 4

5-Mercapto-1-(3-phenoxycarbonamidephenyl)-1,2,3,4-tetrazole (Formula II-17)

24.9 g of 1-(3-aminophenyl)-5-mercaptotetrazole hydrochloride was dispersed in 200 ml of acetonitrile, and 28 ml of triethylamide was added. 15.6 g of phenyl chlorocarbonate was added dropwise at room temperature, followed by stirring for 6 hours at room temperature. 2.2 Liters of water was added, and the crystals which had separated out were filtered off. By recrystallization from acetonitrile, there was obtained 14.7 g of the object product (yield 47%).

m.p.: 190° to 191° C.

The other urethane compounds can be readily synthesized according to the method described in Synthesis Example 4.

The compound of formula II is added in a varied quantity depending on its kind and the layer to which it is added. Usually, it is used in an amount of $10^{-2}$ to $10^2$ moles, and preferably $10^{-1}$ to 10 moles, per 1 mole of silver. These quantities are effective in preventing of changing of photographic characteristics, especially photographic fog, during lapse of time on storage.

The compound of formula II may be added to the layer to which the compound of formula I is added, or may be added to the other layer. The compound of formula II is extremely effective in preventing the fog in the adjacent layer which occurs with the lapse of time as the colloidal silver diffuses into the adjacent layer and acts as the physical developing nucleus. Therefore, it is effective to add to the layer (yellow filter layer and antihalation layer) containing colloidal silver.

The silver halide for the emulsion layer of the color photosensitive material which is used in this invention may be any one of silver bromide, silver iodobromide, silver iodochlorobromide, silver chlorobromide, and silver chloride. The average particle size of the silver halide particles in the photographic emulsion is not specifically limited, however, it preferably is less than 3 μm, and the particle size distribution is not limited. (The average particle size is obtained by projecting the particles and measuring projected areas of particles. The average size is expressed in terms of diameter where the particle is spherical, or in terms of edge length where the particle is cubic.)

The silver halide particles in the photographic emulsion may be regular crystals such as cube and octahedron, or irregular crystals such as sphere and plate. They may also be complex crystals or a mixture of such crystal particles.

The silver halide particles may have internal and surface layers which are different from each other, or may have a uniform single layer. The silver halide particles may be such that the latent image is formed mainly on the surface of the particles, or may be such that the latent image is formed mainly inside the particles.

The photographic emulsion used in this invention can be prepared according to the methods described in Chimie et Physique Photographique, by P. Glafkides, published by Paul Montel in 1967; Photographic Emulsion Chemistry, by G. F. Dufiin, published by The Focul Press in 1966; and Making and Coating Photographic Emulsion, by V. L. Zelikman et al, published by The Focal Press in 1964. In other words, it can be prepared by the acid method, neutral method, or ammonia method. The reaction of soluble silver salt with soluble halide may be performed by adding one component to the other, or by mixing the two components simultaneously, or by the combination of the two methods.

The silver halide particles may be formed in the presence of an excess of silver ions (so called reverse mixing method). The controlled double jet method can also be employed. This is one of the simultaneous mixing methods which keeps pAg constant in the liquid phase in which silver halide is formed. This method provides a silver halide emulsion of substantially uniform regular crystals. The silver halide emulsion may be prepared by mixing two or more silver halide emulsions formed separately.

The silver halide particles may be formed or aged in the presence of cadmium salt, zinc salt, lead salt, thallium salt, iridium salt, iridium complex salt, rhodium salt, rhodium complex salt, iron salt, or iron complex salt.

The method of this invention can be applied to both the negative emulsion that forms the surface latent image and the direct reversal emulsion. The latter emulsion includes the internal latent image emulsion and the prefogged direct reversal emulsion.

The silver halide emulsion of internal latent image type which can be advantageously used in this invention includes, for example, the conversion type emulsion, the core/shell type emulsion, and the emulsion containing a dissimilar metal, which are disclosed in U.S. Pat. Nos. 2,592,250, 3,206,313, 3,447,927, 3,761,276, and 3,935,014.

The typical nucleating agent for these emulsions are hydrazines disclosed in U.S. Pat. Nos. 2,588,982 and 2,563,785; hydrazides and hydrazones disclosed in U.S. Pat. No. 3,227,552; quaternary chlorides disclosed in British Pat. No. 1,283,835, Japanese Patent Publication No. 38164/1974, and U.S. Pat. Nos. 3,734,738, 3,719,494, and 3,615,615; sensitizing dyes containing a substituent having ability of fogging (nucleating) disclosed in U.S. Pat. No. 3,718,470; and acylhydradinophenylthiourea compounds disclosed in U.S. Pat. Nos. 4,030,925 and 4,031,127.

The siler halide emulsion can be used in the form of primitive emulsion which does not undergo chemical sensitizing; but usually it undergoes chemical sensitizing. The chemical sensitizing can be performed according to the methods described in the above-mentioned books written by Glafkides and Zelikman or "Die Grundlagen der Photografischen Prozesse mit Silberhalogeniden", edited by H. Frieser, published by Akademische Verlagsgesselschaft in 1968.

The chemical sensitizing may be accomplished by the sulfur senstization that employs active gelatin or a sulfur compound that reacts with silver ions; the reduction sensitization that employs a reducing substance; and noble metal sensitization that employs gold and other noble metals. They are used individually or in combination with one another.

For sulfur sensitization, thiosulfate salts, thioureas, thiazoles, rhodanines, and other compounds can be used. Examples of such compounds are disclosed in U.S. Pat. Nos. 1,574,944, 2,410,689, 2,278,947, 2,728,668 and 3,656,955.

For reduction sensitization, stannous salts, amines, hydrazine derivatives, formamidine sulfinic acid, and silane compounds can be used. Examples of such compounds are disclosed in U.S. Pat. Nos. 2,487,850, 2,419,974, 2,518,698, 2,983,609, 2,983,610, and 2,694,637.

For noble metal sensitization, complex salts of gold, and compounds of the VIII group in the Periodic Table such as platinum, iridium, and palladium can be used. Examples of such compounds are disclosed in U.S. Pat. Nos. 2,399,083 and 2,448,060 and British Pat. No. 618,061.

The photographic emulsion may undergo spectral sensitization with methyne dyes. Such dyes include cyanine dyes, merocyanine dyes, complex cyanine dyes, complex mercyanine dyes, holopolar cyanine dyes, hemicyanine dyes, styril dyes, and hemioxonol dyes. Particularly useful among them are cyanine dyes, merocyanine dyes, and compound merocyanine dyes.

These useful dyes are disclosed in German Pat. No. 929,080; U.S. Pat. Nos. 2,231,658, 2,493,748, 2,503,776, 2,519,001, 2,912,329, 3,655,394, 3,656,959, 3,672,897, and 3,694,217; British Pat. No. 1,242,588; and Japanese Patent Publication No. 14030/1969.

The color photosensitive material of this invention may have, in addition to the sensitive silver halide emulsion layer, a substantially nonsensitive fine particle silver halide layer which serves for the improvement of graininess and sharpness and for other purposes. Such a nonsensitive layer may be placed on the sensitive silver halide layer or between the sensitive silver halide layer and the colloidal silver layer (yellow filter layer or anti-halation layer).

To increase the sensitivity and contrast and accelerate development, the photosensitive material of this invention may be incorporated with a polyalkylene oxide or a derivative thereof (an ether and an ester amine), a thioether compound, a thiomorpholine compound, a quaternary ammonium salt, an urethane derivative, an urea derivative, an imidazole derivative, or a 3-pyrazolidone compound. Examples of such compounds are disclosed in U.S. Pat. Nos. 2,400,532, 2,423,549, 2,716,062, 3,617,280, 3,772,021, and 3,808,003.

Gelatin can be advantageously used as a binder for the photographic emulsion layers and other layers; but other hydrophilic colloid can also be used. Such substances include, for example, gelatin derivatives, graft polymers of gelatin and other high polymer, and proteins such as alubumin and casein; cellulose derivatives such as hydroxyethyl cellulose, carboxymethylcellulose, and cellulose sulfate ester; a saccharide derivative such as sodium alginate, and a starch derivatives; and a hydrophilic synthetic homopolymer and copolymers such as a polyvinyl alcohol, a partial acetal of polyvinyl alcohol, a poly-N-vinylpyrrolidone, a polyacrylic acid, a polymethacrylic acid, a polyacrylamide, a polyvinylimidazole, and a polyvinyl pyrazole.

Lime-treated gelatin, acid-treated gelatin, enzyme-treated gelatin (as disclosed in Bull. Soc. Phot. Japan, No. 16, p. 30, 1966), and a hydrolyzate or enzymolysis product of gelatin can also be used.

Examples of gelatin derivatives include those compounds obtained by reacting gelatin with an acid halide, acid anhydride, isocyanate, bromoacetic acid, alkane sultone, vinylsulfonamide, maleinimide, polyalkylene oxide, or epoxy compound. They are described in U.S. Pat. Nos. 2,614,928, 3,132,945, 3,186,846, and 3,312,553; British Pat. Nos. 861,414, 1,033,189, and 1,005,784; and Japanese Patent Publication No. 26845/1967.

The above-mentioned gelatin-graft copolymers are prepared by grafting to gelatin a homopolymer or copolymer of a vinyl monomer such as acrylic acid, methacrylic acid, ester or amide thereof, acrylonitrile, and styrene. Preferable among them is a graft polymer which has compatibility with gelatin in some extent such as a polymer of acrylic acid, acrylamide, methacrylamide, hydroxymethacrylate, or methacrylic acid Examples of such graft polymers are disclosed in U.S. Pat. Nos. 2,763,625, 2,831,767, and 2,956,884.

Typical examples of the hydrophilic synthetic polymers are described in West German Patent Application (OLS) No. 2,312,708; U.S. Pat. Nos. 3,620,751 and 3,879,205; and Japanese Patent Publication No. 7561/1968.

The photosensitive material of this invention may be incorporated with a variety of compounds as the antifoggant and stabilizer in addition to or instead of the compound represented by the above-mentioned formula II. Examples of such compounds include azoles such as a benzothiazolium salt, a nitroimidazole, a triazole, a benzotriazole, and a benzimidazole (nitro- or halogen-substituted compound are preferable); heterocyclic mercapto compounds such as a mercaptothiazole, a mercaptobenzothiazole, a mercaptobenzimidazole, a mercaptothiadiazole, a mercaptotetrazole (particularly 1-phenyl-5-mercaptotetrazole), and a mercaptopyrimidine; the above-mentioned heterocyclic mercapto compounds having a water-soluble group such as a carboxyl group and a sulfone group; thioketo compounds such as an oxazolinethion; an azaindenes such as tetraazaindene (particularly 4-hydroxy-substituted (1,3,3a,7)tetraazaindene); a benzenethiosulfonic acid; and a benzenesulfinic acid.

For more detail about examples and usage of these compounds, refer to U.S. Pat. Nos. 3,954,474, 3,982,947, and 4,021,248, and Japanese Patent Publication No. 28660/1977.

The photographic emulsion layers and other layers of the photosensitive material of this invention may contain an inorganic or organic hardening agent. Examples of such hardening agent include chromates (chrome alum, chromium acetate, etc.), aldehydes (formaldehyde, glyoxal, glutaraldehyde, etc.), N-methylol compounds (dimethylol urea, methyloldimethylhydantoin, etc.), dioxane derivatives (2,3-dihydroxydioxane etc.), active vinyl compounds (1,3,5-triacryloyl-hexahydro-S-triazine, 1,3-vinylsulfonyl-2-propanol, etc.), active halogen compounds (2,4-dichloro-6-hydroxy-S-triazine etc.), and mucohalogenic acids (mucochloric acid, mucophenoxychloric acid, etc.). They are used individually or in combination with one another.

The photographic emulsion layers and other layers of the photosensitive material of this invention may contain a variety of surface active agents for the improvement of coatability, antistatic properties, slip properties, emulsification, antiblocking properties, and photographic characteristics (accelerated development, high contrast, senstization, etc.).

Examples of such surface active agents include nonionic surface active agents such as saponin (steroid), alkylene oxide derivatives (e.g., a polyethylene glycol, polyethylene glycol-polypropylene glycol condensate, a polyethylene glycol alkyl ether, a polyethylene glycol alkyl aryl ether, a polyethylene glycol ester, a polyethylene glycol sorbitan ester, a polyalkylene glycol alkylamine or -amide, and a silicone-polyethylene oxide adduct), glycidol derivatives (e.g., an alkenylsuccinic acid polyglyceride and an alkylphenol polyglyceride), fatty acid esters of a polyhydric alcohol, and sugar alkyl esters; anionic surface active agents containing an acid group (carboxyl group, sulfo group, phospho group, sulfate ester group, phosphate ester group, etc.) such as an alkylcarboxylate, an alkylsulfonate, an alkylbenzenesulfonate, an alkylnaphthalenesulfonate, an alkyl sulfate ester, an alkyl phosphate ester, an N-acyl-N-alkyltaurine acid, a sulfosuccinate ester, a sulfoalkylpolyoxyethylene alkylphenyl ether, and a polyoxyethylene alkylphosphate ester; amphoteric surface active agents such as an amino acid, an aminoalkylsulfonic acid, an aminoalkylsulfuric acid, a phosphate ester, an alkylbetaine, and an amineoxide; cationic surface active agents such as an alkylamine salt, an aliphatic or aromatic quaternary ammonium salt, a heterocyclic quanternary ammonium salt (pyridinium, imidazolium, etc.), and a phosphonium or phosphonium salt containing an aliphatic group or a heterocyclic group.

The photographic emulsion layer of the photosensitive material of this invention may contain color forming couplers. The coupler is a compound which develops color through oxidation coupling with the aromatic primary amine developing agent (e.g., phenylenediamine derivative and aminophenol derivative) in the color development process. The magenta coupler includes, for example, 5-pyrazolone couplers, pyrazolobenzimidazole couplers, cyanoacetylcoumarone couplers, and open chain acylacetonitrile couplers. The yellow coupler includes acylacetoamide couplers, e.g., benzoyl acetanilides and pivaloylacetanilides. The cyan coupler includes naphthol couplers and phenol couplers. These couplers preferably is of non-diffusion type which has a hydrophobic group called ballast group. Either a two-equivalent coupler and a four-equivalent coupler will do. The coupler may be a colored coupler which has the color correction effect, or may be a so-called DIR coupler which releases a development inhibitor as development proceeds. In addition, a colorless DIR coupling compound which forms a colorless coupling reaction product and releases a development inhibitor or DIR redox compound may almost be used.

Examples of magenta couplers are disclosed in U.S. Pat. Nos. 2,600,788, 2,983,608, 3,062,653, 3,127,269, 3,311,476, 3,419,391, 3,519,429, 3,558,319, 3,582,322, 3,615,506, 3,834,908, and 3,891,445; West Germany Pat. No. 1,810,464; West Germany Patent Application (OLS) Nos. 2,408,665, 2,417,945, 2,418,959, and 2,424,467; Japanese Patent Publication No. 6031/1965; and Japanese Laid-open Pat. Nos. 20826/1976, 13041/1975, 58922/1977, 129538/1974, 74027/1974, 159336/1975, 42121/1977, 74028/1974, 60233/1975, 26541/1976, 55122/1978, and 118034/1980.

Examples of yellow couplers are disclosed in U.S. Pat. Nos. 2,875,057, 3,265,506, 3,408,194, 3,551,155, 3,582,322, 3,725,072, 3,891,445, 3,894,875, and 4,157,919; West Germany Pat. No. 1,547,868; West Germany Patent Application (OLS) Nos. 2,219,917, 2,261,361, and 2,414,006; British Pat. No. 1,425,020; Japanese Patent Publication No. 10788/1976; and Japanese Patent Laid-open Nos. 26133/1972, 73147/1973, 102636/1976, 6341/1975, 123342/1975, 130442/1975, 21827/1976, 87650/1975, 82424/1977, 115219/1977, and 82332/1978.

Examples of cyan couplers are disclosed in U.S. Pat. Nos. 2,369,929, 2,434,272, 2,474,293, 2,521,908, 2,895,296, 3,034,892, 3,311,476, 3,458,315, 3,476,563, 3,583,971, 3,591,383, 3,767,411, 4,004,929, and 4,124,396; West Germany Patent Application (OLS) Nos. 2,414,830 and 2,454,329; Japanese Patent Laid-open Nos. 59838/1973, 26034/1976, 5055/1973, 146828/1976, 69624/1977, 90932/1977, 65134/1981, 29235/1981, and 99341/1981.

Examples of colored couplers are disclosed in U.S. Pat. Nos. 3,476,560, 2,521,908, and 3,034,892; Japanese Patent Publication Nos. 2016/1969, 22335/1963, 11304/1967, and 32461/1969; Japanese Patent Laid-open Nos. 26034/1976 and 42121/1977; and West Germany Patent Application (OLS) No. 2,418,959.

Examples of DIR couplers include o-aminoazo type DIR couplers as disclosed in U.S. Pat. No. 3,148,062; thioether type DIR couplers as disclosed in U.S. Pat. No. 3,227,554; 2-benzotriazolyl type DIR couplers as disclosed in U.S. Pat. No. 3,617,291; 1-benzotriazolyl type DIR couplers as disclosed in West Germany Patent Application (OLS) No. 2,414,006 and Japanese Patent Laid-opne Nos. 82424/1977 and 117627/1977; nitrogen-containing heterocyclic ring substituted acetate ester type DIR couplers as disclosed in Japanese Patent Laid-open Nos. 30591/1975 and 82423/1977; two-equivalent type DIR cyan couplers as disclosed in West Germany Patent Application (OLS) No. 2,527,652, and Japanese Patent Laid-open Nos. 90932/1977 and 146828/1976; malonic acid diamide type DIR coupler as disclosed in Japanese Patent Laid-open No. 69624/1977; and DIR coupler having the timing adjusting releasing group as disclosed in U.S. Pat. No. 4,248,962 and "Research Disclosure" No. 21228.

Examples of colorless DIR coupling compounds include thioether type cyclic colorless DIR coupling compounds as disclosed in British Pat. No. 1,423,588; West German Patent Application (OLS) Nos. 2,405,442, 2,523,705, 2,529,350, and 2,448,063; and U.S. Pat. No. 3,938,996; thioether type linear colorless DIR coupling compounds as disclosed in U.S. Pat. Nos.

3,632,345 and 3,928,041; benzotriazolyl type colorless DIR coupling compounds as disclosed in Japanese Patent Laid-Open Nos. 147716/1975, 105819/1976, and 67,628/1977; and picolinium type colorless DIR coupling compounds as disclosed in Japanese Patent Laid-Open No. 72,433/1976.

Examples of DIR redox compounds include DIR hydroquinones as disclosed in U.S. Pat. Nos. 3,639,417 and 3,297,445, and West German Patent Application (OLS) No. 2,460,202; and DIR redox type couplers as disclosed in Japanese Patent Laid-Open No. 57828/1977.

The photosensitive material of this invention may contain the developing agent such as disclosed in "Research Disclosure" Vol. 176, p. 29, Section "Developing Agents".

In the case of the photosensitive material of this invention, the photographic emulsion layers and other layers may contain a dye for various purposes, e.g., as filters and for irradiation prevention.

Examples of such dyes are disclosed in "Research Disclosure" Vol. 176, pp. 25-26, Section "Absorbing and Filter Dyes".

The photosensitive material of this invention may contain an antistatic agent, plasticizer, matting agent, lubricant, UV absorber, fluorescent brightener, and aerial fogging preventing agent.

The silver halide emulsion layers and/or other layers may be coated on the base according to the method as disclosed in "Research Disclosure" Vol. 176, pp. 27-28, Section "Coating Procedures".

The color photosensitive material having the above-mentioned features undergoes the following fundamental processing after exposure when used as color negative film, color positive film, or color paper. Color development—stopping—washing—bleach acceleration bath—washing—bleaching with persulfate—washing—fixing—washing—stabilization—drying. This processing may further include the prebath and hardening bath before color development. Washing after stopping, bleach acceleration bath and bleaching with persulfate may be omitted. The bleach acceleration bath may be omitted.

The color photosensitive material undergoes the following processing after exposure when used as color reversal film. Black and white development—stopping—washing—fogging—washing—color development—stopping—washing—bleach acceleration bath—washing—bleaching with persulfate—washing—fixing—washing—stabilization—drying. This processing may further include the prebath, prehardening bath, and neutralizing bath. Washing after stopping, fogging, bleach accelerating bath, and bleaching may be omitted. The fogging may be substituted by re-exposure or may be omitted by adding a fogging agent to the color development bath. The bleach acceleration bath may be omitted.

The color developing solution is usually an alkaline aqueous solution containing the color developing agent which may be a known primary aromatic amine developing agent. Examples of such developing agent include phenilene diamines such as 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfoneamideethylaniline, and 4-amino-3-methyl-N-ethyl-N-$\beta$-methoxyethylaniline. Other examples are disclosed in "Photographic Processing Chemistry" by F. A. Mason, pp. 226-229, published by Focal Press in 1966; U.S. Pat. Nos. 2,193,015 and 2,592,364; and Japanese Patent Laid-Open No. 64933/1973.

The color developing solution may contain a pH buffer such as an alkali metal sulfite, carbonate, borate, and phosphate, and an antifoggant such as a bromide and an iodide and an organic antifoggant. The color developing solution may contain, as occasion demands, a water softener; a preservative such as hydroxylamine; an organic solvent such as benzyl alcohol and diethylene glycol; a development accelerator such as a polyethylene glycol, a quaternary ammonium salt, and an amine; a color forming coupler; a competing coupler; a fogging agent such as sodium borohydride; an auxiliary developing agent such as 1-phenyl-3-pyrazolidone; thickener; a polycarboxylic acid type chelating agent as disclosed in U.S. Pat. No. 4,083,623; and antioxidant as disclosed in West German Patent Application (OLS) No. 2,622,950.

After color development, the photographic emulsion layers undergo bleaching with a persulfate salt. This bleaching process may be carried out simultaneously with or independently from the fixing process.

The persulfate salt used as a bleaching agent in this invention is an alkali metal persulfate such as potassium persulfate and sodium persulfate, or ammonium persulfate.

The bleaching agent is preferably used in an amount of 0.05 to 2 moles for 1 liter of bleaching solution.

As a re-halogenizing agent the bleaching solution may contain a chloride such as potassium chloride, sodium chloride, and ammonium chloride, or a bromide such as potassium bromide, sodium bromide, and ammonium bromide. The use of a bromide may be impractical because it gives off bromine gas. The above-mentioned halide is preferably used in an amount of 0.1 to 2 moles for 1 liter of a bleaching solution. In addition, the bleaching solution may be incorporated with a pH buffer, which is an inorganic or organic acid and a salt thereof, such as boric acid, borax, sodium metaborate, acetic acid, sodium acetate, sodium carbonate, potassium carbonate, phosphorous acid, phosphoric acid, sodium phosphate, citric acid, sodium citrate, and tartaric acid. The bleaching solution may be incorporated with sodium sulfate or potassium sulfate for adjusting the concentrations of salts in the bleaching solution.

The bleaching solution may be incorporated with an imide compound in an amount of $2 \times 10^{-6}$ to $1 \times 10^{-1}$ moles, preferably $1 \times 10^{-2}$ to $4 \times 10^{-2}$ moles, for 1 liter of a bleaching solution in order to prevent generation of halogen gas, as disclosed in Japanese Patent Laid-Open No. 149944/1980.

The pH of the bleaching solution is preferably adjusted to 1.0 to 7.0, and more preferably to 1.5 to 3.5.

The bleaching solution of this invention or the prebath thereof may contain a bleaching accelerating agent, although it is not essential. Examples of such an agent are mercapto compounds and dithiocarbamate compounds as disclosed in U.S. Pat. Nos. 3,707,374, 3,772,020, and 3,893,858; Japanese Patent Publication No. 28227/1976; Japanese Patent Laid-Open Nos. 94927/1978 and 95631/1978; Japanese Patent Application Nos. 97980/1978 and 98901/1978; and "Research Disclosure" No. 15704 (May 1977).

The fixer of common composition can be used. The fixing agent is a thiosulfate, thiocyanate, or organic sulfur compound. The fixer may contain a water-soluble aluminum salt as a hardening agent.

The invention is described in more detail with reference to the following examples.

EXAMPLE 1

A multi-layer color photosensitive material made up of a cellulose triacetate film base and the layers of compositions shown hereinbelow.

Layer 1: Antihalation layer
  Composition: 1 kg of black colloidal silver emulsion (containing 15 g of blackened silver and 100 g of gelatin in 1 kg of emulsion) and 40 cc of 5 wt% aqueous solution of sodium p-dodecylbenzenesulfonate (coating aid).

The mixture was coated so that the dried layer was 2 μm thick.

Layer 2: Gelatin intermediate layer
  Thickness of dried layer: 1.0 μm

Layer 3: Red sensitive slow silver halide emulsion layer
  Composition: 1 kg of silver iodobromide (containing 5 mol% of iodine) emulsion containing 100 g of silver halide and 70 g of gelatin in 1 kg of emulsion and having the average particle size of 0.3 μm. 210 cc of 0.1% methanol solution of anhydro-5,5-dichloro-9-ethyl-3,3'-di(3-sulfopropyl)thiacarbocyaninehydrosulfide pyridinium salt (as a red sensitive spectral sensitizer). 20 cc of 5 wt% aqueous solution of 5-methyl-7-hydroxy-2,3,4-triazaindolizine.

400 g of cyan coupler emulsion (1) of the following formulation.

200 g of cyan coupler emulsion (2) of the following formulation.

200 cc of 2% aqueous solution of colored cyan coupler (CC-1).

30 cc of 2 wt% aqueous solution of 2-hydroxy-4,6-dichlorotriazine sodium salt as a gelatin hardener.

This solution was coated so that the dried layer was 3.5 μm thick.

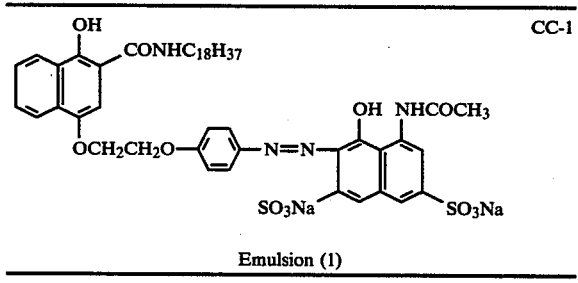

CC-1

Emulsion (1)

| | | | |
|---|---|---|---|
| <1> | 10 wt % aqueous solution of gelatin | 1000 | g |
| <2> | Sodium p-dodecylbenzenesulfonate | 5 | g |
| | Tricresyl phosphate | 60 | cc |
| | Cyan coupler (C-101) | 70 | g |
| | Ethyl acetate | 100 | cc |

The four components of <2> were previously dissolved at 55° C. and then added to the component <1> previously heated to 55° C., followed by emulsification by a colloid 10 mill.

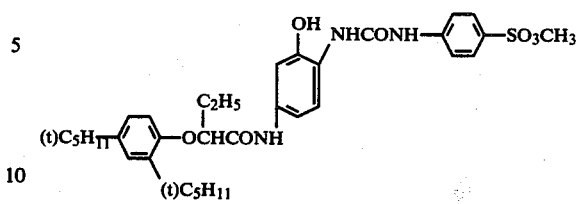

C-101

Emulsion (2)

| | | | |
|---|---|---|---|
| <1> | 10 wt % aqueous solution of gelatin | 1000 | g |
| <2> | Sodium p-dodecylbenzenesulfonate | 5 | g |
| | Tricresyl phosphate | 60 | cc |
| | Cyan coupler (C-101) | 70 | g |
| | DIR compound (D-1) | 10 | g |
| | Ethyl acetate | 100 | cc |

The five components of <2> were previously dissolved at 55° C. and then added to the component <1> previously heated to 55° C., followed by emulsification by a colloid mill.

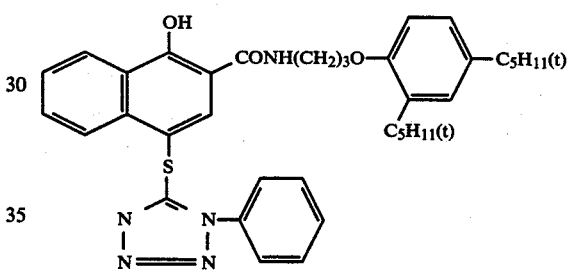

D-1

Layer 4: Red sensitive high-speed silver halide emulsion layer
  Composition: Same as the silver halide emulsion of layer 3 except the following change.

| | |
|---|---|
| Average particle size of emulsion | 0.9 μm |
| Red sensitive sensitizer | 140 cc |
| Emulsion (1) | 220 g |
| Emulsion (2) | 30 g |

The silver halide emulsion was coated so that the dried layer was 2.2 μm thick.

Layer 5: Gelatin intermediate layer
  Thickness of dried layer: 0.8 μm

Layer 6: Green sensitive slow silver halide emulsion layer
  Composition: 1 kg of silver iodobromide emulsion (same as used for Layer 3).

180 cc of 0.1% methanol solution of 3,3'-di(2-sulfoethyl)-9-ethylbenzooxacarbocyanine pyridinium salt (as a green sensitive sensitizing dye).

20 cc of 5 wt% aqueous solution of 5-methyl-7-hydroxy-2,3,4-triazaindolizine.

320 g of magenta coupler emulsion (3) of the following formulation.

180 g of magenta coupler emulsion (4) of the following formulation.

50 cc of 2 wt% aqueous solution of 2-hydroxy-4,6-dichlorotriazine sodium salt as a gelatin hardener.

This solution was coated so that the dried layer was 3.2 μm thick.

Layer 7: Green sensitive high-speed silver halide emulsion layer
  Composition: Same as the silver halide emulsion of Layer 6 except the following change.

| Average particle size of emulsion | 1.0 μm |
| --- | --- |
| Content of iodine in emulsion | 6.5 mole % |
| Green sensitive sensizer | 100 cc |
| Emulsion (3) | 150 g |
| Emulsion (4) | 30 g |

The silver halide emulsion was coated so that the dried layer was 2.2 μm thick.

| Emulsion (3) | | |
| --- | --- | --- |
| <1> | 10 wt % aqueous solution of gelatin | 1000 g |
| <2> | Sodium p-dodecylbenzenesulfonate | 5 g |
|  | Tricresyl phosphate | 80 cc |
|  | Magenta coupler (M-101) | 70 g |
|  | Colored magenta coupler (CM-1) | 10 g |
|  | Ethyl acetate | 120 cc |

The five components of <2> were previously dissolved at 55° C. and then added to the component <1> previously heated to 55° C., followed by emulsification by a colloid mill.

ously heated to 55° C., followed by emulsification by a colloid mill.

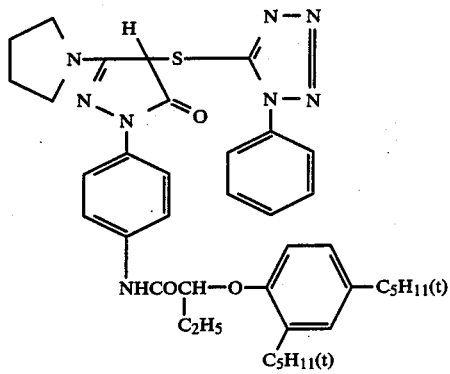

D-2

Layer 8: Yellow colloidal silver layer
  (Thickness of dried layer: 1.6 μm)

Layer 9: Blue sensitive slow silver halide emulsion layer
  Composition: 1 kg of silver iodobromide emulsion (same as used for Layer 3 except that the average particle size is 0.5 μm).
  20 cc of 5 wt% aqueous solution of 5-methyl-7-hydroxy-2,3,4-triazaindolizine.
  1500 g of yellow coupler emulsion (5) of the following formulation.

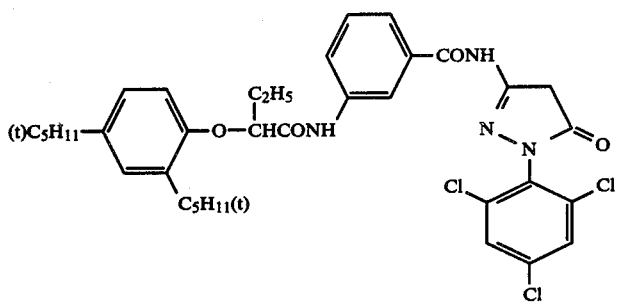

M-101

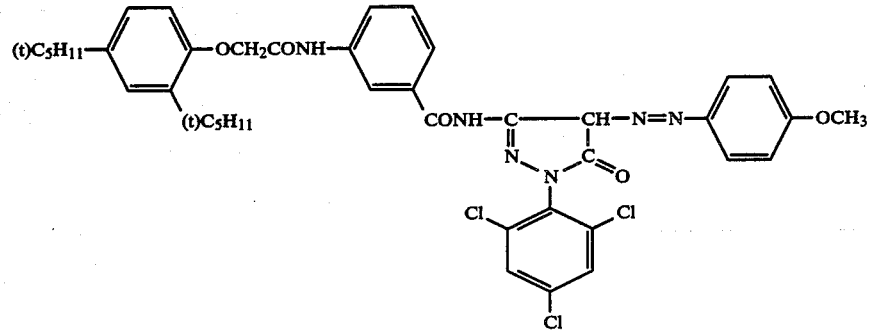

CM-1

| Emulsion (4) | | |
| --- | --- | --- |
| <1> | 10 wt % aqueous solution of gelatin | 1000 g |
| <2> | Sodium dodecylbenzene sulfonate | 5 g |
|  | Tricresyl phosphate | 80 cc |
|  | Magenta coupler (M-101) | 50 g |
|  | Colored magenta coupler (CM-1) | 10 g |
|  | DIR compound (D-2) | 15 g |
|  | Ethyl acetate | 120 cc |

The six components of <2> were previously dissolved at 55° C. and then added to the component <1> previously 50 cc of 2 wt% aqueous solution of 2-hydroxy-4,6-dichlorotriazine sodium salt as a gelatin hardener.

This solution was coated so that the dried layer was 3.0 μm thick.

| Emulsion (5) | | |
|---|---|---|
| <1> | 10 wt % aqueous solution of gelatin | 1000 g |
| <2> | Sodium dodecylbenzene sulfonate | 5 g |
| | Tricresyl phosphate | 80 cc |
| | Yellow coupler (Y-1) | 100 g |
| | Ethyl acetate | 120 cc |

The four components of <2> were previously dissolved at 55° C. and then added to the component <1> previously heated to 55° C., followed by emulsification by a colloid mill.

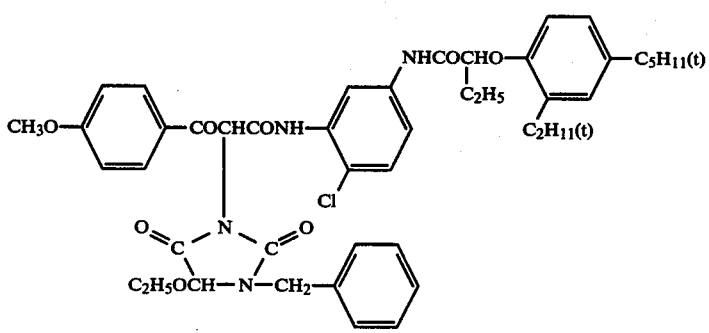

Y-1

Layer 10: Blue sensitive high-speed silver halide emulsion layer
  Composition: Same as the silver halide emulsion for Layer 9 except the following change.

| Average particle size of emulsion: | 1.1 μm |
|---|---|
| Emulsion (5) | 300 g |

The silver halide emulsion was coated so that the dried layer was 2.5 μm thick.
Layer 11: Gelatin protective coat
  (Thickness of dried layer: 1.5 μm)

The photographic film prepared as above was designated as sample film 1.

The emulsion for the antihalation layer was incorporated with 1 wt% aqueous solution of the compound of this invention in varied quantities as shown in Table 1. The compounds used were I-1, I-3, I-5, I-7, I-9, I-12, and I-13. The resulting photographic films were designated as sample films 2 to 15.

The sample films 1 to 15 were exposed by using an optical wedge and then subjected to the following development processing. After the processing, the quantity of remaining silver (fresh) was determined. The results are shown in Table 1.

| Processing | Temperature | Time |
|---|---|---|
| Color development | 41° C. | 3 minutes |
| Stopping | 38° C. | 30 seconds |
| Washing | 38° C. | 30 seconds |
| Bleach acceleration | 38° C. | 30 seconds |
| Bleaching | 38° C. | 1 minute or 3 minutes |
| Washing | 38° C. | 1 minute |
| Fixing | 38° C. | 2 minutes |
| Washing | 38° C. | 2 minutes |
| Stabilizing bath | 38° C. | 10 seconds |

The processing solutions used have the following compositions.

| Color development solution: | |
|---|---|
| Sodium hydroxide | 2 g |
| Sodium sulfite | 2 g |
| Potassium bromide | 1.4 g |
| Sodium chloride | 1 g |
| Borax | 1 g |
| Hydroxylamine sulfate | 4 g |
| Disodium ethylenediaminetetraacetate | 2 g |
| 4-amino-3-methyl-N—ethyl-N—(β-hydroxyethyl)aniline monosulfate | 4 g |
| Water qs to | 1 liter |

| Stopping solution: | |
|---|---|
| Water | 800 ml |
| Glacial acetic acid | 30 ml |
| Sodium hydroxide | 1.65 g |
| Water qs to | 1 liter |
| Bleach acceleration bath: | |
| Sodium sulfite (anhydrous) | 9.0 g |
| 2-N,N—dimethylaminoethyl-isothiourea dihydrochloride | 2.5 g |
| Sodium acetate | 8.0 g |
| Glacial acetic acid | 2.3 ml |
| Water qs to | 1 liter |
| Bleaching solution: | |
| Sodium persulfate | 60 g |
| Sodium chloride | 20 g |
| Sodium dihydrogenphosphate | 15 g |
| Sodium tetrapolyphosphate | 2 g |
| β-alanine | 2 g |
| Phosphoric acid (85%) | 2.2 ml |
| Water qs to | 1 liter |
| Fixing solution: | |
| Sodium thiosulfate | 150 g |
| Sodium sulfite (anhydrous) | 15 g |
| Borax | 12 g |
| Glacial acetic acid | 15 ml |
| Water qs to | 1 liter |
| Stabilizing bath: | |
| Formaldehyde (37%) | 10 ml |
| Water qs to | 1 liter |

TABLE 1

| Sample film No. | Compound (I) | Quantity added (mg/m$^2$) | Total silver coated (g/m$^2$) | Silver remaining after development processing Bleaching (1 minute) (μg/cm$^2$) | Bleaching (3 minutes) (μg/cm$^2$) |
|---|---|---|---|---|---|
| 1 | — | — | 7.5 | 17 | 2.5 |
| 2 | I-1 | 1.77 | 7.5 | 13 | 2.1 |
| 3 | I-1 | 3.55 | 7.5 | 6 | 1.7 |
| 4 | I-3 | 1.83 | 7.5 | 14 | 2.2 |
| 5 | I-3 | 3.65 | 7.5 | 8 | 1.8 |
| 6 | I-5 | 1.55 | 7.5 | 12 | 1.9 |
| 7 | I-5 | 3.09 | 7.5 | 5 | 1.7 |

TABLE 1-continued

| Sample film No. | Compound (I) | Quantity added (mg/m²) | Total silver coated (g/m²) | Silver remaining after development processing | |
|---|---|---|---|---|---|
| | | | | Bleaching (1 minute) (μg/cm²) | Bleaching (3 minutes) (μg/cm²) |
| 8 | I-7 | 1.76 | 7.5 | 13 | 2.2 |
| 9 | I-7 | 3.51 | 7.5 | 7 | 1.9 |
| 10 | I-9 | 1.20 | 7.5 | 13 | 2.1 |
| 11 | I-9 | 2.40 | 7.5 | 8 | 1.8 |
| 12 | I-12 | 1.00 | 7.5 | 12 | 2.1 |
| 13 | I-12 | 2.00 | 7.5 | 6 | 1.8 |
| 14 | I-13 | 1.21 | 7.5 | 13 | 2.0 |
| 15 | I-13 | 2.41 | 7.5 | 7 | 1.7 |

It is to be noted from Table 1 that the desilvering is remarkably promoted when the compound of formula I of this invention is added to the antihalation layer and the bleaching time can be reduced. The same effect was obtained when the compound of formula I was added to other layers than the antihalation layer.

EXAMPLE 2

Sample films were prepared in the same manner as in Example 1, except that the yellow filter layer was incorporated with the compound of formula II in an amount of 2.1 moles for 1 mole of colloidal silver, as shown in Table 2.

Sample films were also prepared in the same manner as in Example 1, except that the yellow filter layer was incorporated with 1-phenyl-5-mercaptotetrazole which is a known antifoggant.

Sample films as prepared in Example 1 were used as control.

These sample films were subjected to accelerated aging tests under the following storage conditions.

(1) Storage at room temperature: 3 days
(2) Storage at 50° C. and 60 %RH: 3 days
(3) Storage at 45° C. and 80 %RH: 3 days Subsequently, the sample films were exposed by using an optical wedge and subjected to development processing in the same manner as in Example 1. After bleaching for 3 minutes, the density of the sample films was measured and there was obtained the characteristic curve of the green sensitive layer adjacent to the yellow filter layer. Thus the minimum density $D_{min}$ and relative logarithmic sensitivity $S_{0.2}$ of the green sensitive layer were determined. (The relative logarithmic sensitivity was determined according to the exposure that gives a density of fog plus 0.2.) Table 2 shows $D_{min}$ and $S_{0.2}$ which vary depending on the storage conditions.

The minimum density of yellow color which was developed after bleaching for 3 minutes or 1 minute was measured in order to evaluate the desilvering rate of yellow colloidal silver in the sample film. The greater the difference between the density measured after bleaching for 3 minutes and the density measured after bleaching for 1 minute, the more the yellow colloidal silver remaining in the photosensitive material. The results are shown in Table 3.

TABLE 2

| Sample film No. | Film No. in Example 1 | Antifoggant added to yellow filter layer | $D_{min}$ in green sensitive layer | | | $S_{0.2}$ in green sensitive layer | | |
|---|---|---|---|---|---|---|---|---|
| | | | Storage condition (1) | Storage condition (2) | Storage condition (3) | Storage condition (1) | Storage condtion (2) | Storage condition (3) |
| 20 | 6 | Blank | 0.57 | 0.56 | 0.64 | −2.08 | −2.10 | −1.91 |
| 21 | 6 | 1-phenyl-5-mercaptotetrazole | 0.52 | 0.52 | 0.57 | −2.11 | −2.10 | −1.90 |
| 22 | 6 | II - 2 | 0.52 | 0.50 | 0.54 | −2.13 | −2.12 | −1.98 |
| 23 | 6 | II - 12 | 0.52 | 0.51 | 0.53 | −2.12 | −2.12 | −1.99 |
| 24 | 12 | Blank | 0.57 | 0.56 | 0.65 | −2.09 | −2.09 | −1.92 |
| 25 | 12 | 1-phenyl-5-mercaptotetrazole | 0.52 | 0.51 | 0.58 | −2.12 | −2.11 | −1.91 |
| 26 | 12 | II - 1 | 0.52 | 0.51 | 0.54 | −2.13 | −2.13 | −1.99 |
| 27 | 12 | II - 17 | 0.52 | 0.50 | 0.53 | −2.12 | −2.14 | −2.00 |

TABLE 3

| Sample film No. | Film No. in Example 1 | Antifoggant added to yellow filter layer | Minimum density of yellow color development | | | | | |
|---|---|---|---|---|---|---|---|---|
| | | | Bleaching for 1 minute | | | Bleaching for 3 minutes | | |
| | | | Storage condition (1) | Storage condition (2) | Storage condition (3) | Storage condition (1) | Storage condition (2) | Storage condition (3) |
| 20 | 6 | Blank | 1.16 | 1.15 | 1.23 | 1.15 | 1.14 | 1.21 |
| 21 | 6 | 1-phenyl-5-mercaptotetrazole | 1.16 | 1.15 | 1.18 | 1.10 | 1.10 | 1.12 |
| 22 | 6 | II - 2 | 1.11 | 1.10 | 1.12 | 1.09 | 1.10 | 1.09 |
| 23 | 6 | II - 12 | 1.11 | 1.10 | 1.12 | 1.10 | 1.10 | 1.10 |
| 24 | 12 | Blank | 1.16 | 1.15 | 1.21 | 1.15 | 1.14 | 1.20 |
| 25 | 12 | 1-phenyl-5-mercaptotetrazole | 1.16 | 1.15 | 1.19 | 1.10 | 1.11 | 1.13 |
| 26 | 12 | II - 1 | 1.11 | 1.10 | 1.12 | 1.10 | 1.09 | 1.09 |
| 27 | 12 | II - 7 | 1.12 | 1.11 | 1.12 | 1.10 | 1.10 | 1.10 |

It is to be noted from Tables 2 and 3 that the occurrence of fog in the green sensitive layer is remarkably reduced during storage (particularly under high humidity), when the compound of formula I is added to the antihalation layer and the compound of formula II is added to the yellow filter layer. Moreover, this effect does not interfere with the desilvering effect achieved by the compound of formula I.

EXAMPLE 3

Sample films were prepared by coating the following layers on the cellulose acetate base coated with a subbing layer.

Layer 1: Antihalation layer

Same as Layer 1 in Example 1.
Layer 2: Intermediate layer
Same as Layer 2 in Example 1.
Layer 3: Red sensitive slow silver halide emulsion layer
Same as Layer 3 in Example 1.
Layer 4: Red sensitive medium-speed silver halide emulsion layer
The same silver halide emulsion as used for Layer 3 was used with the following change.

| Average particle size of emulsion: | 0.7 μm |
|---|---|
| Red sensitive color sensitizer | 200 cc |
| Emulsion (1) | 300 g |
| Emulsion (2) | 80 g |

The resulting silver halide emulsion was coated so that the dried layer was 1.8 μm thick.
Layer 5: Red sensitive high-speed silver halide emulsion layer
Same as Layer 4 in Example 1.
Layer 6: Gelatin intermediate layer
Same as Layer 5 in Example 1.
Layer 7: Green sensitive slow silver halide emulsion layer
Same as Layer 6 in Example 1.
Layer 8: Green sensitive medium-speed silver halide emulsion layer
The same silver halide emulsion as used for Layer 7 was used with the following change. t,0670
The resulting silver halide emulsion was coated so that the dried layer was 1.3 μm

| Average particle size of emulsion: | 0.7 μm |
|---|---|
| Green sensitive color sensitizer | 170 cc |
| Emulsion (3) | 200 g |
| Emulsion (4) | 50 g |

Layer 9: Green sensitive high-speed silver halide emulsion layer
Same as Layer 7 in Example 1.
Layer 10: Yellow Colloidal silver layer
Same as Layer 8 in Example 1.
Layer 11: Blue sensitive slow silver halide emulsion layer
Same as Layer 9 in Example 1.
Layer 12: Blue sensitive medium-speed silver halide emulsion layer
The same silver halide emulsion as used for Layer 11 was used with the following change.

| Average particle size of emulsion: | 0.5 μm |
|---|---|
| Emulsion (5) | 480 g |

The resulting silver halide emulsion was coated so that the dried layer was 1.4 μm thick.
Layer 13: Blue sensitive high-speed silver halide emulsion layer
Same as Layer 10 in Example 1.
Layer 14: Gelatin protective layer
Same as Layer 11 in Example 1.
The photographic film thus prepared was designated as sample film No. 30. As in Example 1, the antihalation layer of the sample film No. 30 was incorporated with 0.1 wt% aqueous solution of the compound of formula I in an amount as shown in Table 4. The resulting films were designated as sample film Nos. 31 to 44.

The sample film Nos. 30 to 44 were exposed by using a stepped optical wedge and then subjected to the same development processing as in Example 1. The quantity of silver remaining after processing was determined. The results are shown in Table 4.

TABLE 4

| Sample film No. | Compound (I) | Quantity added (mg/m$^2$) | Total silver coated (g/m$^2$) | Silver remaining after development processing Bleaching (1 minute) (μg/cm$^2$) | Bleaching (3 minutes) (μg/cm$^2$) |
|---|---|---|---|---|---|
| 30 | — | — | 9.1 | 38 | 15 |
| 31 | I-1 | 1.77 | 9.1 | 24 | 8.0 |
| 32 | I-1 | 3.55 | 9.1 | 19 | 5.5 |
| 33 | I-2 | 1.99 | 9.1 | 26 | 8.5 |
| 34 | I-2 | 3.99 | 9.1 | 21 | 6.0 |
| 35 | I-5 | 1.55 | 9.1 | 30 | 10 |
| 36 | I-5 | 3.09 | 9.1 | 23 | 6.5 |
| 37 | I-6 | 2.10 | 9.1 | 30 | 10 |
| 38 | I-6 | 4.21 | 9.1 | 23 | 7.0 |
| 39 | I-8 | 2.26 | 9.1 | 31 | 11 |
| 40 | I-8 | 4.52 | 9.1 | 24 | 8.0 |
| 41 | I-10 | 1.41 | 9.1 | 26 | 9.5 |
| 42 | I-10 | 2.81 | 9.1 | 22 | 7.0 |
| 43 | I-12 | 1.00 | 9.1 | 25 | 9.0 |
| 44 | I-12 | 2.00 | 9.1 | 20 | 6.5 |

It is to be noted from Table 4 that the desilvering is remarkably promoted when the desilvering accelerating agent of this invention is added to the antihalation layer and the bleaching time can be reduced.

While the invention has been described in detail and with reference to specific embodiments thereof, it will be apparent to one skilled in the art that various changes and modifications can be made therein without departing from the spirit and scope thereof.

What is claimed is:

1. A method for bleaching a color photosensitive material, which comprises exposing imagewise a silver halide color photosensitive material, performing color development, and bleaching the color photosensitive material with a processing solution containing a persulfate, said silver halide color photosensitive material containing at least one compound selected from the group consisting of the compounds represented by formula I, salts thereof, and precursors thereof which cleaves under an acid or alkaline processing solution to form a compound represented by the formula I:

Formula I where $R^1$ and $R^2$ each independently represents a hydrogen atom, an aliphatic group, or $R^1$ and $R^2$ together form a ring together with the N atom; $R^3$ represents —$R^4$— or —$R^4$—S—, said —$R^4$— being a divalent aliphatic group; and X represents a divalent heterocyclic ring group containing at least one atom selected from the group consisting of a nitrogen atom, an oxygen atom, and a sulfur atom.

2. A method for bleaching a color photosensitive material as recited in claim 1, wherein $R^3$ in formula I represents —$R^4$—S—, said —$R^4$— being a divalent aliphatic group.

3. A method for bleaching a color photosensitive material as recited in claim 1, wherein the silver halide color photosensitive material contains at least one compound from the group consisting of compounds represented by formula I and wherein the silver halide color photosensitive material contains at least one compound selected from the group consisting of compounds represented by formula II, the salt thereof, and the precursor thereof which cleaves under an alkaline processing solution represented by the formula II:

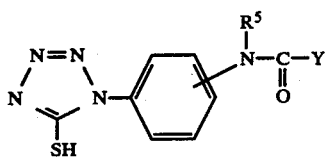

Formula II where Y represents —NR$^6$R$^7$ or —OR$^8$; R$^5$, R$^6$, and R$^7$ each independently represents a hydrogen atom, a substituted and unsubstituted aliphatic group, a substituted or unsubstituted aromatic group; and R$^8$ represents a substituted or unsubstituted aliphatic group or a substituted or unsubstituted aromatic group; or R$^5$ and R$^8$ together form a ring containing oxygen and nitrogen; or R$^6$ and R$^7$ together form a five-membered or six-membered heterocyclic ring with the nitrogen atom.

4. A method for bleaching a color photosensitive material as recited in claim 3, wherein R$^3$ in formula I represents —R$^4$—S—, said —R$^4$— being a divalent aliphatic group.

5. A method for bleaching a color photosensitive material as recited in claim 3, wherein Y in formula II represents —NR$^6$R$^7$.

6. A method for bleaching a color photosensitive material as recited in claim 3, wherein Y in formula II represents —OR$^8$.

7. A method for bleaching a color photosensitive material as recited in claim 1, wherein R$^1$ and R$^2$ each represents a substituted and unsubstituted alkyl group, alkenyl group and alkynyl group.

8. A method for bleaching a color photosensitive material as recited in claim 7, wherein the substituent of said substituted groups is selected from the group consisting of phenyl group, a substituted phenyl group, an alkoxy group, an alkylthio group, hydroxy group, carboxy group, sulfo group, an alkylamino group and an amido group.

9. A method for bleaching a color photosensitive material as recited in claim 1, wherein R$^1$ and R$^2$ form at least one of 5-membered and 6-membered heterocyclic ring containing a nitrogen atom.

10. A method for bleaching a color photosensitive material as recited in claim 1, wherein said heterocyclic ring further contains at least one atom selected from the group consisting of nitrogen atom and oxygen atom.

11. A method for bleaching a color photosensitive material as recited in claim 9, wherein R$^1$ and R$^2$ form a ring selected from the group consisting of

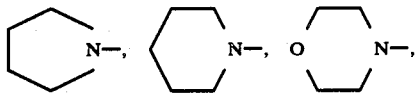

-continued

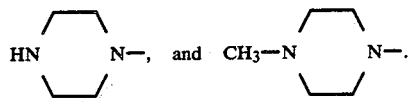

12. A method for bleaching a color photosensitive material as recited in claim 4, wherein said R$^4$ represents a divalent aliphatic group selected from the group consisting of substituted and unsubstituted linear and branched aliphatic hydrocarbon and a divalent aliphatic group containing an ether bond in the carbon chain thereof.

13. A method for bleaching a color photosensitive material as recited in claim 1, wherein X represents a divalent heterocyclic ring group selected from the group consisting of a tetrazole, a triazole, a triadiazole, an oxadizole, an imidazole, a thiazole, an oxazole, a benzimidazole, a benzothiazole and a benzoxazole rings.

14. A method for bleaching a color photosensitive material as recited in claim 1, wherein said salt is a compound selected from the group consisting of a metal salt, a quaternary ammonium salt, a quaternary phosphonium salt, hydrochloride, sulfate, p-toluenesulfonate and methanesulfonate.

15. A method for bleaching a color photosensitive material as recited in claim 1, wherein said compound represented by the formula I is contained in the color photosensitive material in an amount of $1 \times 10^{-7}$ to $1 \times 10^{-3}$ mole per 1 m$^2$ of the support of the color photosensitive material.

16. A method for bleaching a color photosensitive material as recited in claim 1, wherein said color photosensitive material contains silver in an amount of more than 30 mg/100 cm$^2$.

17. A method for bleaching a color photosensitive material as recited in claim 2, wherein R$^5$, R$^6$, R$^7$ and R$^8$ each represents an aliphatic group have 1-8 carbon atoms and said aliphatic group is selected from the group consisting of alkyl group and alkenyl group.

18. A method for bleaching a color photosensitive material as recited in claim 2, wherein R$^5$, R$^6$, R$^7$ and R$^8$ each represents an aryl group having 6-20 carbon atoms.

19. A method for bleaching a color photosensitive material as recited in claim 2, wherein R$^6$ and R$^7$ form a heterocyclic ring having 2-10 carbon atoms.

20. A method for bleaching a color photosensitive material as recited in claim 2, wherein said salt is a compound selected from the group consisting of a metal salt, a quaternary ammonium salt and a quaternary phosphonium salt, hydrochloride, sulfate, p-toluenesulfonate and methanesulfonate.

21. A method for bleaching a color photosensitive material as recited in claim 2, wherein said compound represented by formula II is contained in the color photosensitive material in an amount of $1 \times 10^{-2}$ to $1 \times 10^2$ moles per 1 mole of silver.

22. A method for bleaching a color photosensitive material as recited in claim 2, wherein said compound represented by formula II is contained in the same layer in the photosensitive material where the compound represented by formula I is contained.

23. A method for bleaching a color photosensitive material as recited in claim 2, wherein said compound represented by formula II is contained in a layer in the photosensitive layer other than the layer wherein the compound represented by formula I is contained.

* * * * *